US006645503B1

(12) United States Patent
Arumugham et al.

(10) Patent No.: US 6,645,503 B1
(45) Date of Patent: Nov. 11, 2003

(54) ANTIGENIC CONJUGATES OF CONSERVED LIPOPOLYSACCHARIDES OF GRAM NEGATIVE BACTERIA

(75) Inventors: Rasappa G. Arumugham, Pittsford, NY (US); Maria Fortuna-Nevin, Webster, NY (US); Michael A. Apicella, Solon, IA (US); Bradford W. Gibson, Berkeley, CA (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 09/264,747

(22) Filed: Mar. 9, 1999

Related U.S. Application Data (60) Provisional application No. 60/088,364, filed on Mar. 10, 1998.

(51) Int. Cl.[7] .................... A61K 39/385; A61K 39/38; A61K 39/116; A61K 39/02; A61K 39/095
(52) U.S. Cl. .................... 424/197.11; 424/194.1; 424/193.1; 424/184.1; 424/203.1; 424/234.1; 424/250.1; 514/23; 514/54; 536/123.1
(58) Field of Search .................... 424/250.1, 249.1, 424/251.1, 256.1, 257.1, 258.1, 260.1, 261.1, 241.1, 236.1, 234.1, 184.1, 193.1, 194.1, 197.11, 203.1, 282.1, 823, 826, 832, 831, 179.1, 178.1, 183.1; 514/54, 23, 916, 898, 921; 536/1.11, 123.1; 530/807, 825; 435/181

(56) References Cited

U.S. PATENT DOCUMENTS

| 4,707,543 A | * | 11/1987 | Zollinger et al. ............ 530/402 |
| 4,912,094 A | * | 3/1990 | Myers et al. .................. 514/54 |
| 4,929,604 A | * | 5/1990 | Munford et al. .............. 514/53 |
| 6,207,157 B1 | * | 3/2001 | Gu et al. .................. 424/184.1 |

FOREIGN PATENT DOCUMENTS

| WO | WO 94/08021 | * | 4/1994 |
| WO | WO 9719688 | * | 6/1997 |

OTHER PUBLICATIONS

Campnagari et al. Microbial Pathogenesis 8 (5): 353–362, abstract, 1990.*
Tyler et al. Am. J. Vet. Res. 49 (11): 1950–1954, 1988.*
Davis et al. J. Exp. Med. 147 (4): 1007–1017, 1978.*
Zeigler et al. New Eng. J. Med. 307: 1225–1230, 1982.*
Tyler et al. J. Vet. Intern. Med. 4: 17–25, 1990.*
McLaughlin et al. J. Bacteriol. 174: 6455–6459, 1992.*
Lindberg et al. In: New Approaches to Stabilization of Vaccine Potency. (Ed) Brown F. Dev. Biol. Basel, Karger, 87: 59–71, 1996.*
Lambden et al. J. Immunol. Methods 48: 233–240, 1982.*
Green et al., Vaccines94. (Ed) Norrby et al. Cold Spring Harbor Laboratory Press, pp. 125–129, 1994.*
Lugowski et al. FEMS Immunol. Med. Microbiol. 16: 21–30, Novem. 1996.*
Mironova et al. Zh. Mikrobiol. Epidemiol. Immunobiol. 4: 58–62, 1988.*
Hill et al. J. Med. Microbiol. 21: 25–33, 1986.*
Lees et al. Infect. Immun. 63: 2508–2516, 1995.*
Gupta et al. Infect. Immun. 60: 3201–3208, 1992.*
Lugowski et al. J. Immunol. Methods 95: 187–194, 1986.*
Tomita et al. J. Dairy Sci. 78:2178–2185, 1995.*
Tomita et al. J. Dairy Sci. 76: Suppl. 1, abstract P36G, 1993.*
Tomita GM. Immunization of dairy cows against coliform mastitis. Dissertation. The Ohio University, pp. 1–109, 1994.*
Jachymek W. Postepy Hig. Med. Dosw. 49: 171–178, abstract, 1995.*
Preston, A. et al., *Critical Reviews in Microbiology*, 22:(3):139–180 (1996).
Phillips, N. J. et al., *Biochemistry*, 31:4515–4526 (1992).
John, C. M. et al., *J. Biol. Chem.*, 266:19303–19311 (1991).
Kniskern, P. J. et al., *Vaccine Design*, Chapter 30:673–694 (1995).
Eby, R., *Vaccine Design*,, Chapter 31:695–718 (1995).
Jennings, H. J. et al., *Infect. Immun.*, 43(1):407–412 (1984).
Verheul, A. F. M. et al., *Infect. Immun.*, 61(1):187–196 (1993).
Verheul, A. F. M. et al., *Infect. Immun.*, 59(3):843–851 (1991).
Gu, X–X. et al., *Infect. Immun.*, 61(5):1873–1880 (1993).
Bhattacharjee, A. K. et al., *J. Infect. Dis.*, 173:1157–1163 (1996).
Gu, X–X. et al., *Infect. Immun.*, 64(10):4047–4053 (1996).

* cited by examiner

*Primary Examiner*—S. Devi
(74) *Attorney, Agent, or Firm*—Thomas S. Szatkowski; Michael R. Nagy (57) ABSTRACT

Antigenic conjugates are provided which comprise a carrier protein covalently bonded to the conserved portion of a lipopolysaccharide of a gram negative bacteria, wherein the conserved portion of the lipopolysaccharide comprises the inner core and lipid A portions of the lipopolysaccharide, the conjugate eliciting a cross reactive immune response against heterologous strains of the gram negative bacteria.

8 Claims, 4 Drawing Sheets

FIG. 1A

AN O-ANTIGEN OR REPEATING POLYSACCHARIDE

FIG. 1B

HEPTAACYL LIPID A

FIG. 1C

*Neisseria* CORE LOS STRUCTURE

FIG. 2A

*Haemophilus* CORE LOS STRUCTURE

FIG. 2B

*Haemophilus influenzae* STRAIN 2019 LOS

FIG. 3A

*Neisseria gonorrhoeae* STRAIN 1291 LOS

FIG. 3B

| LANE # | SAMPLE |
|---|---|
| 1 | BRL LOWS |
| 2 | SAMPLE blk |
| 3 | N. mening A1 |
| 4 | NTHi TN106 |
| 5 | NTHi P860295 |
| 6 | N. gc 52407 P+ |
| 7 | N. gc 1756 P+ |
| 8 | H. pylori 1103 |
| 9 | H. pylori 43579 |
| 10 | H. pylori 1105 |
| 11 | M. cat 1230:359 |
| 12 | M. cat 25238 |
| 13 | M. cat 430:345 |
| 14 | N.gc LB2 |
| 15 | N.gc Pgh3-1 |

WESTERN BLOT ANALYSIS OF ANTI LOS-CONJUGATE
SERA AGAINST LOS FROM DIFFERENT BACTERIA

FIG. 4

ANTIGENIC CONJUGATES OF CONSERVED LIPOPOLYSACCHARIDES OF GRAM NEGATIVE BACTERIA

CROSS REFERENCE TO RELATED APPLICATIONS

This application claims the benefit of U.S. Provisional Application No. 60/088,364 which was converted from U.S. patent application Ser. No. 09/037,529, filed Mar. 10, 1998, pursuant to a petition filed under 37 C.F.R. 1.53(c)(2) filed May 6, 1998.

FIELD OF THE INVENTION

This invention relates to antigenic conjugates of the conserved portion of the lipopolysaccharides of certain gram negative bacteria and to vaccines containing such antigenic conjugates. The conjugates elicit antibodies which exhibit cross reactivity against heterologous strains of gram negative bacteria and the vaccines containing such conjugates induce antibodies which are functional and protective against such gram negative bacterial organisms.

BACKGROUND OF THE INVENTION

Figure 1A:
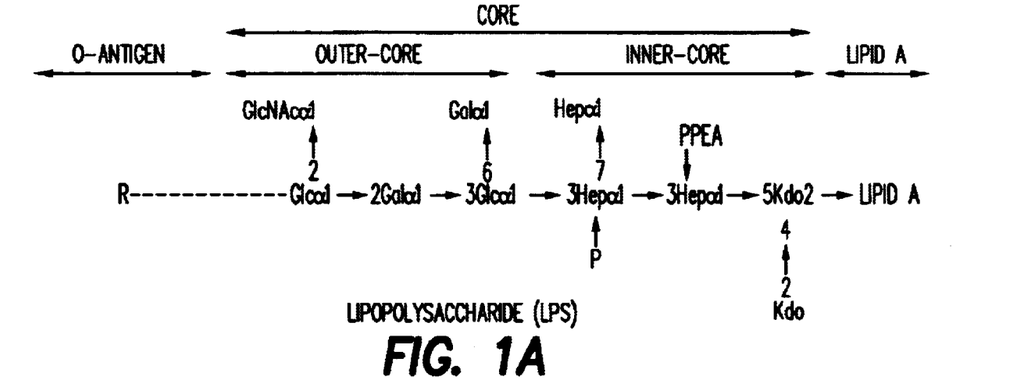
FIG. 1A shows the typical structure of the lipid A-inner core of *Salmonella typhimurium*.
Figure 1B:
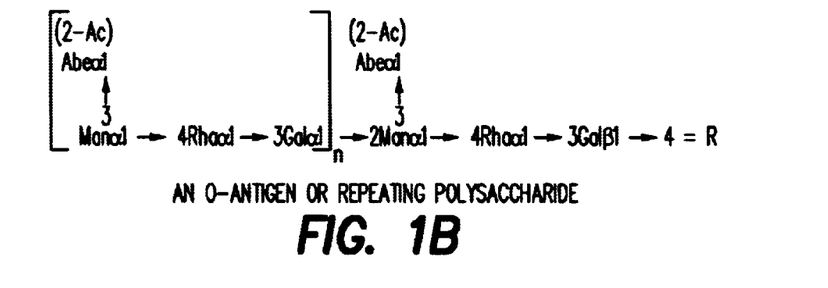
FIG. 1B shows the typical structures of the O-antigen or repeating polysaccharide of *Salmonella typhimurium*.
Figure 1C:
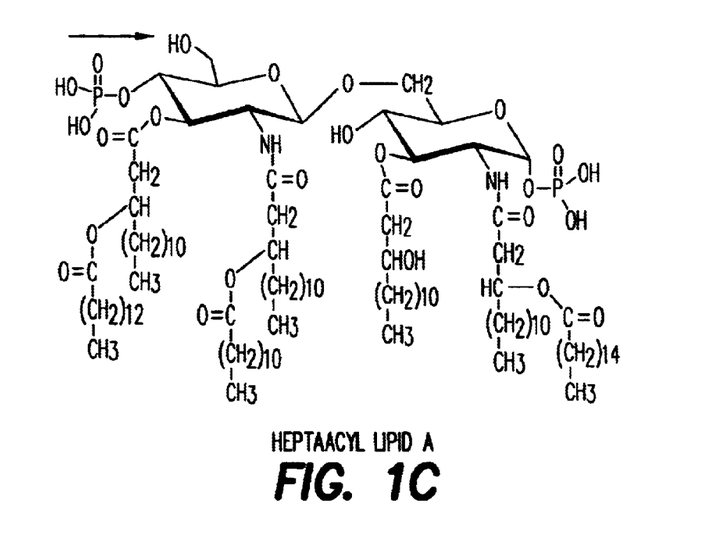
FIG. 1C shows a structure for the heptaacyl Lipid A of *Salmonella typhimurium*.

Lipopolysaccharides (LPS) are major surface antigens localized abundantly on the surface of gram negative bacteria. LPS molecules are comprised of: (1) a lipid A portion which consists of a glucosamine disaccharide substituted with phosphates, phosphoethanolamine groups and long chain fatty acids in ester and amide linkages; (2) an inner core portion attached to the lipid A portion by an eight carbon sugar, ketodeoxyoctonoate (KDO), which may be substituted by 1 to 2 additional KDO molecules and by up to 3 heptose moieties; (3) an outer core portion comprising hexoses such as glucose, galactose, N-acetylglucosamine and N-acetylgalactosamine; and (4) an O-specific chain comprising repeating oligo-saccharide units which vary widely among bacterial strains. Polymerization of these repeating units to structures in excess of 60,000 daltons is not uncommon. The LPS molecules can vary extensively at the structural and antigenic level among bacterial strains, although the structure of the inner core is largely conserved among bacterial species. A typical structure of the lipid-A inner core of *Salmonella typhimurium* LPS is illustrated in FIG. 1. The immune response responsible for the evolution of naturally protective antibodies is considered to arise by natural immunization to this region of the LPS.

In non-enteric pathogens, the LPS structure lacks repeating O-antigen units. Moreover, the complete genetic machinery for assembly of the O-antigen repeating unit appears to be absent in such pathogens. This has led to the designation of these LPS structures as lipooligosaccharides (LOS). There are similarities between LPS and LOS structures in such pathogens. For instance, all of the LPS and LOS structures link the lipid A regions to the cores through the KDO junction. The number of KDO residues can vary from one (e.g., *Haemophilus influenzae* and *Haemophilus ducreyi*) to two (e.g., *Neisseria meningitidis* and *Neisseria gonorrhoeae*). Recent studies indicate that the branched oliogsaccharides are synthesized separately from the core region and the assembly of the entire LOS structure is completed on the outer side of the cytoplasmic membrane (see Preston, et al., "The Lipooligosaccharides of Pathogenic Gram-Negative Bacteria", *Critical Reviews In Microbiology*, 22:139–180 (1996)).

Figure 2A:
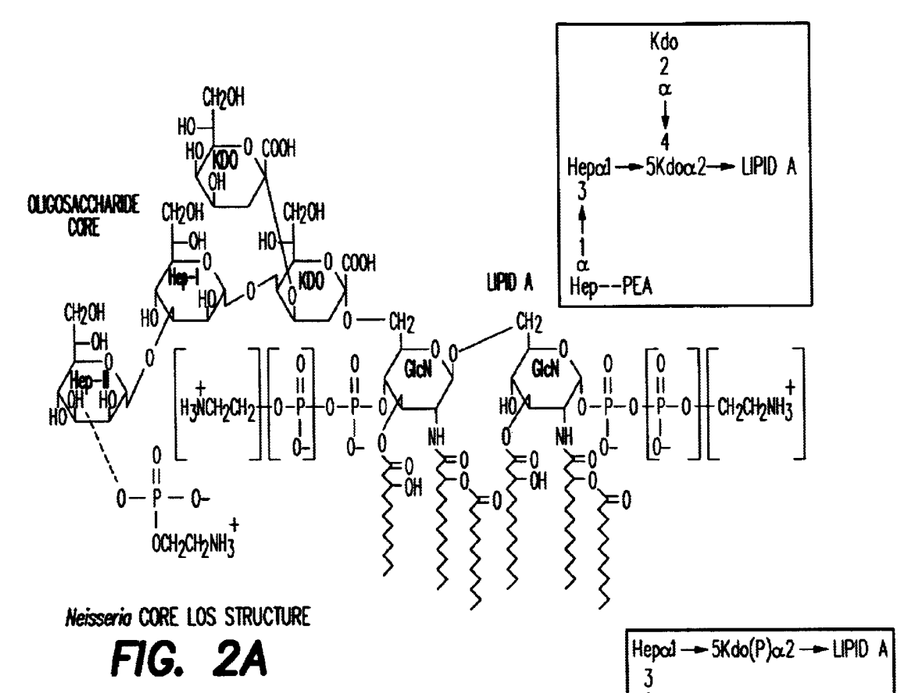
FIG. 2A shows the core LOS structure of Haemophilus species.
Figure 2B:
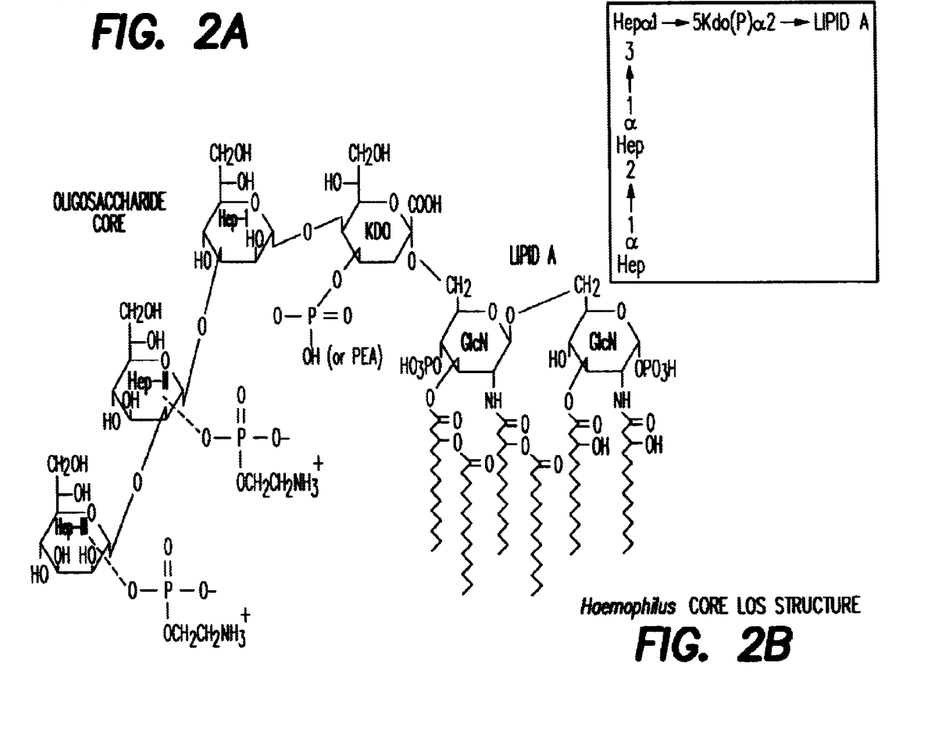
FIG. 2B shows the core LOS structure of Neisseria species.
Figure 3A:
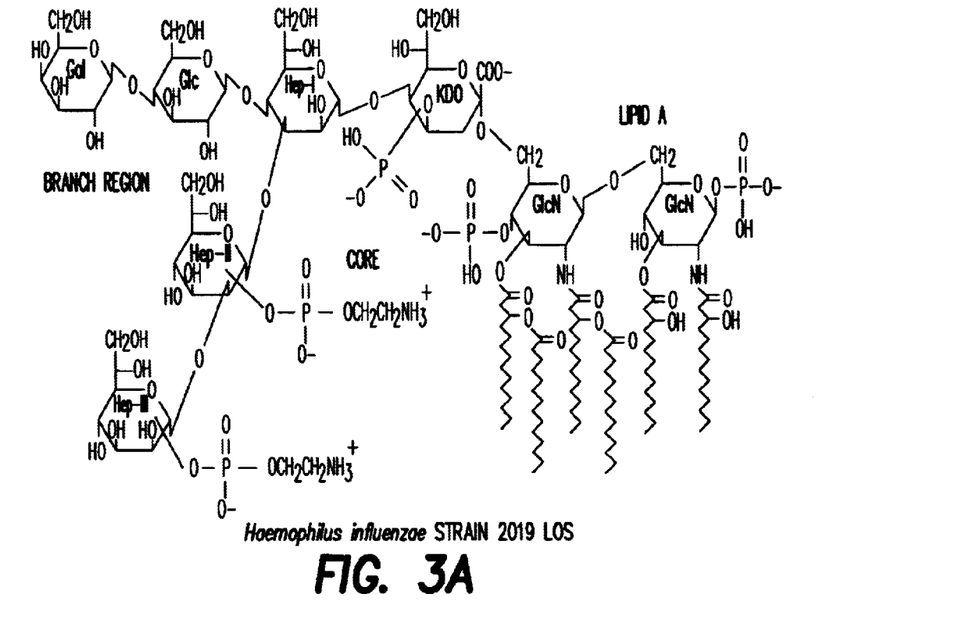
FIG. 3A shows the LOS structure of *Haemophilus influenzae* strain 2019.
Figure 3B:
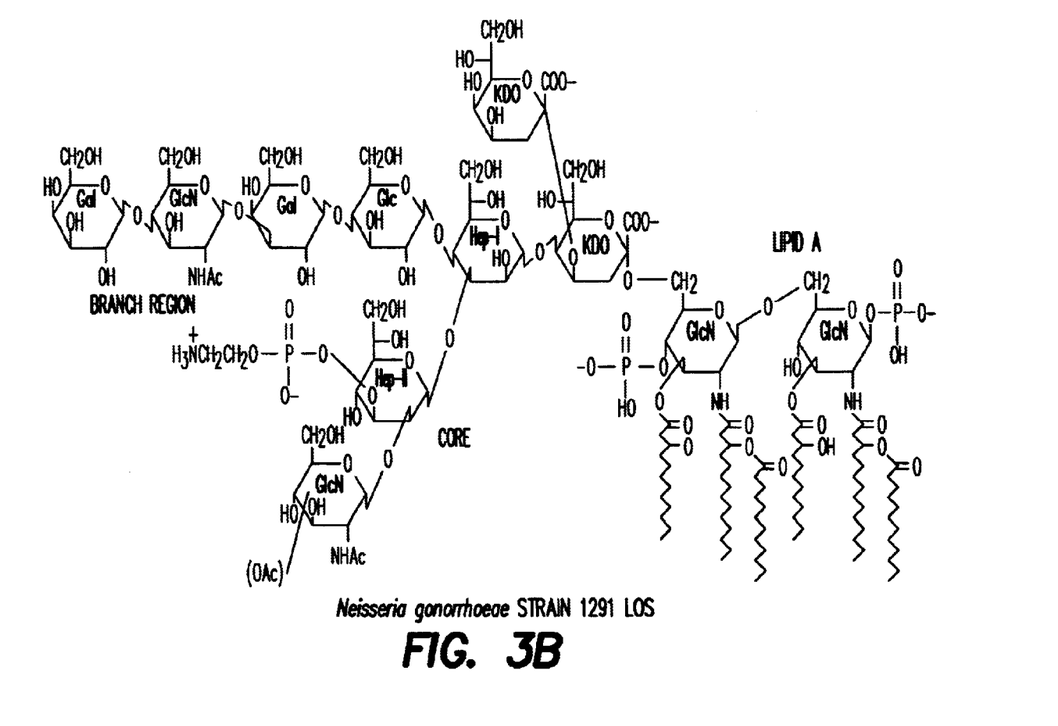
FIG. 3B shows the LOS structure of *Neisseria gonorrhoeae* strain 1291.

Accordingly, there is a single core region in such LOS structures without a distinct inner and outer core region. The core structure of these pathogens can vary from species to species and may comprise KDO in the complete absence of heptose (e.g., *Moraxella catarrhalis*); KDO in the presence of a di-heptose structure (e.g., *Neisseria meningitidis* and *Neisseria gonorrhoeae*); or KDO in the presence of a tri-heptose structure (e.g., *Haemophilus influenzae* and *Haemophilus ducreyi*). Examples of core structures from Haemophilus and Neisseria are shown in FIG. 2. The oligosaccharide units can extend from each of the heptoses and/or they can be substituted by phosphoethanolamine groups. Typical examples of completed LOS structures of *Haemophilus influenzae* strain 2019 (see Phillips et al., "Structural Characterization of the Cell Surface Lipooligosaccharides from a Non-Typable Strain of *Haemophilus Influenzae*," *Biochemistry*, 31:4515–4526 (1992)) and *Neisseria gonorrhoeae* strain 1291 (see John et al., "The Structural Bases for Pyocin Resistance in *Neisseria gonorrhoeae* lipooligosaccharides," *J. Biol. Chem.*, 266:1903–1911 (1991)) are shown in FIG. 3.

The use of LPS in the development of vaccines is known in the art. It has long been recognized that a specific antibody response directed against the LPS of a particular bacterial pathogen can contribute to protection against that specific strain. It is further known that saccharide structures (e.g., the saccharide portions of LPS) can be conjugated to a carrier protein, so that a vaccine composition containing such a conjugate will elicit the desired T-dependent response. An example of this is the successful glycoconjugate vaccines against bacteria having type-specific capsular saccharides see, *Vaccine Design: The Subunit and Adjuvant Approach*, Powell, M. F., and Newman, M. J., 673–694 (1995). This category of immune response is the basis for the effectiveness in human infants of a new generation of saccharide-protein conjugate vaccines as discussed in *Vaccine Design: The Subunit and Adjuvant Approach*, Powell, M. F., and Newman, M. J., 695–718 (1995).

However, since the LPS of heterologous strains of such pathogens demonstrate extensive variation of the outer core saccharide and/or O-specific chain, efforts to generate an antibody response to a number of heterologous strains or heterologous genera of bacteria utilizing a vaccine containing a single LPS have to date been unsuccessful.

In an effort to develop an LPS-based vaccine against *Neisseria meningitidis*, tetanus toxoid has been conjugated with oligosaccharides isolated from the LPS of a number of *Neisseria meningitidis* strains (see, Jennings et al., *Infect. Immun.*, 43:407–412 (1984)). However, the antibodies elicited by this conjugate were oligosaccharide specific and exhibited a high degree of serotype specificity.

Verheul et al., *Infect. Immun.*, 61:187–196 (1993), disclose the conjugation of oligosaccharides of meningococcal LPS to either tetanus toxoid or meningococcal outer membrane protein. In mice, the tetanus toxoid conjugates induced oligosaccharide specific antibodies which were not bactericidal against meningococci. The outer membrane protein—LPS conjugates induced antibodies against the outer membrane protein, but not against LPS. Verheul et al., *Infect. Immun.*, 59:843–851 (1991), also studied the immunogenicity of the conjugates of oligosaccharides of several *Neisseria meningitidis* strains and tetanus toxoid in rabbits. The results demonstrated that the antibodies elicited are directed only towards the oligosaccharide portion of the LPS which contain the immunotype specific epitopes.

The preparation of oligosaccharides from the LPS of *Neisseria meningitidis* laboratory adapted wild strain A1 and the subsequent conjugation thereof to tetanus toxoid as the carrier protein was disclosed in Gu et al., *Infect. Immun.*, 61:1873–1880 (1993). The conjugates were immunogenic in mice and rabbits and the majority of the antibodies were directed against immunotype-specific LPS epitopes. Also, the conjugate antisera showed less cross reactivity to different immunotypes of LPS than the LPS antisera. These studies demonstrate that LPS-derived oligosaccharide conjugates induce antibodies to the specific oligosaccharide immunotype. However, there was no evidence that the conjugate induced significant cross reactive antibodies to a common core saccharide structure present in the majority of *Neisseria meningitidis* strains.

Bhattacharjee et al., *J. Infect. Dis.*, 173:1157–1163 (1996) disclosed the mixture of the LPS from *Escherichia coli* with the outer membrane protein of *Neisseria meningitidis* group B, resulting in the formation of unconjugated, non-covalent complexes thereof. It was found that these complexes elicited antibodies which cross reacted with a number of gram negative bacteria. However, no evidence was provided to indicate that these complexes had properties different from other preparations of unconjugated saccharide structures which are known to be incapable of eliciting a T-dependent antibody response which can be boosted upon administration of subsequent doses. Moreover, it is known that such unconjugated saccharides do not elicit an appropriate immune response in infants.

Gu et al., *Infect. Immun.*, 64:4047–4053 (1996) disclose the preparation of conjugates of oligosaccharides from non-typeable *Haemophilus influenzae* and tetanus toxoid. However, the antisera induced in rabbits demonstrated bactericidal activity against only homologous strains.

Accordingly, there remains a need for antigenic conjugates and vaccines containing such conjugates which effectively induce an immunogenic response, preferably a T-dependent response, to a given species of gram negative bacteria, as well as which exhibit effective cross reactivity to heterologous strains or serotypes of gram negative bacteria within a given genus. Moreover, it would be advantageous for such conjugates and vaccines to elicit antibodies which exhibit cross reactivity to heterologous genera of gram negative bacteria.

SUMMARY OF THE INVENTION

The present invention is directed to antigenic conjugates comprising a carrier protein covalently bonded to the conserved LPS portion of a gram negative bacteria, wherein the conserved portion of the LPS comprises at least the conserved inner core and the lipid A portion of the LPS. The conjugate elicits a cross reactive immune response against heterologous strains of gram negative bacteria and preferably, against heterologous genera of gram negative bacteria.

The present invention is further directed to vaccines comprising these antigenic conjugates and methods for immunizing individuals with such vaccines to prevent various diseases caused by gram negative bacteria.

DETAILED DESCRIPTION OF THE INVENTION

The present invention is directed to antigenic conjugates of a carrier protein and the conserved LPS of gram negative bacteria and vaccines containing such conjugates. The present conjugates utilize the LPS of various gram negative bacteria including, but not limited to: *Neisseria meningitidis, Neisseria gonorrhoeae, Haemophilus influenzae*, non-typeable *Haemophilus influenzae, Haemophilus ducreyi, Helicobacter pylori, Escherichia coli, Chlamydia, Salmonella, Salmonella typhimurium, Salmonella minnesota, Proteus mirabilis, Pseudomonas aeruginosa, Moraxella catarrhalis, Bordetella pertussis*, Shigella, Klebsiella, and *Vibrio cholerae*.

The present conjugates and the vaccines containing these conjugates generate a functional polyclonal antibody response against the conserved LPS portion contained in the conjugates. Thus, the vaccines are capable of reacting to a large number of heterologous strains of pathogens, thereby inducing a cross reactive and cross-functional antibody response against different strains of gram negative bacteria. This cross reactive response is demonstrated both against heterologous strains within a given genus, as well as against heterologous genera of gram negative bacteria.

The present invention is thus directed to antigenic conjugates which generate an antibody response against the common conserved portions of the LPS of a gram negative bacteria, i.e., portions of the LPS which are common to a number of gram negative bacteria. As used herein, the term "LPS" is meant to include both smooth LPS and LOS (otherwise known as "rough LPS").

As noted above, the LPS of gram negative bacteria comprise the inner core portion, the Lipid A portion, the outer core portion and the O-specific antigen. In order to elicit a response to heterologous strains or genera of bacteria, the structure of the inner core and lipid A portions must be conserved and utilized in the present conjugates. Accordingly, the term "conserved portion" of LPS as used herein is meant to include at least the glucosamine disaccharide substituted with phosphates, phosphoethanolamine groups and long chain fatty acids in ester and amide linkages (i.e., the lipid A portion); and the KDO function of the inner core and the heptose substituents, if any. The phosphates, phosphoethanolamine and pyrophosphoethanolamine groups which may be contained in the inner core may also be included in the "conserved portion", although they may not be necessary. The portion of the pathogen contained in the "conserved portion" is highly conserved among bacterial strains and thus, broadly cross reactive antibodies can arise from these structures (see, e.g., Apicella et al., "The Normal Human Serum Bactericidal Antibody Response to the Lipooligosaccharide of *Neisseria gonorrhoeae*", *J. Infect. Dis.*, 153:520–528 (1986).

It is further within the scope of the present invention that additional branched carbohydrates of the inner core of LPS-bearing strains or oligosaccharides of LOS-bearing strains, may be conserved as part of the "conserved portion" as defined herein. This, however, is not required or even desirable in many instances.

It has been found by the present inventors that the generation of a conjugate utilizing such a conserved portion of the LPS structure elicits a boostable, T-cell dependent IgG response in the individual being treated and that the resultant antibodies cross react to the surface of heterologous strains within a particular bacterial genus, as well as to heterologous genera of gram negative bacteria. Moreover, the surface reactive antibodies elicited by the present conjugates have been found to be both bactericidal (i.e., demonstrating a functional property associated with immunoprotection) and protective.

The conserved portions of the LPS utilized in the present conjugates may be prepared by a number of techniques known to those skilled in the art. For example, the conserved structure may be prepared by: (1) the chemical synthesis of whole or part of the conserved core structure, (2) the selection of wild type strains that will produce LPS which contains predominantly the conserved structure, (3) the enzymatic cleavage of non-reducing sugar residues of LPS synthesized by wild type strains, and (4) the synthesis of the conserved structure of the LPS of a given bacterial organism by various mutants and progenies derived from those mutants such as disclosed in PCT Application Publication No. WO97/19688 (e.g., the production of the conserved core portion of *Neisseria meningitidis* LPS by mutant strains defective in the biosynthesis of LPS; the production of core-defective rough mutants of Salmonella and *Escherichia coli* by their exposure to bacteriophages; the production of *Neisseria gonorrhoeae* LPS mutants by the exposure of wild type strains to pyocin and the progenies derived from these mutants; the generation of transposan-induced mutations of specific enzymes involved in the biosynthesis of LPS; and the site-directed mutations of specific enzymes involved in LPS biosynthesis and the progenies derived from those mutant strains).

The preferred means of preparing the conserved portions of the LPS for use in the present conjugates is through the synthesis of the LPS conserved portion via mutant bacterial strains and their progeny (pathway 4 above). More preferably, the following mutant strains are utilized to synthesize the LPS conserved portion: organisms that express only the conserved core saccharides of the LPS, such as the $R_a$ core (both inner and outer core) of Salmonella, $R_c$ and $R_e$ of Salmonella and $J_5$ of *Escherichia coli*; organisms that do not add glucose to the core portion of the LPS; organisms that do not add galactose to the core portion of the LPS, such as the strain 281.25 mutant from *Haemophilus influenzae* type b as described in *Biochemistry*, 35:5837–5947 (1996); organisms that do not add glucose to the core portion of the LPS due to mutations in the phosphoglucomutase (PGM) gene, such as the NMB R6 strain of *Neisseria meningitidis* and 1291-R6 strain of Neisseria gonorrhoeae discribed in *J. Biol. Chem.*, 269:11162–11169 (1994); organisms that do not add galactose to the core portion of the LPS due to mutations in the galactose epimerase (GalE) gene, such as the mutant strain SS3 of *Neisseria meningitidis* described in *Infect. Immun.*, 63:2508–2515 (1995); and organisms that do not add glucose or galactose to the core portion of the LPS due to mutations in the corresponding transferase enzymes, such as mutations in the corresponding transferase enzyme, such as mutations in the glucosyl or galactosyl transferase genes described in *J. Exp. Med.*, 180:2181–2190 (1994).

Studies by Lee et al., *Infect. Immun.*, 63:2508–2515 (1995) have shown that a mutation in galactose epimerase results in the expression of LPS which is truncated after the outer core or branch regions containing glucose. A screening of Tn916-generated mutants of group B *Neisseria meningitidis* showed that a stable LPS mutant strain (designated NMB-R6 strain) expressed a deep core LPS with the structure: GlcNAc-Hep$_2$(PEA)-KDO$_2$-LipidA. Additional studies have shown that transposon is inserted into the putative phospho-glucomutase gene (see *J. Biol. Chem.*, 269:11162–11169 (1994)). The cell free extracts of the mutant strain demonstrated no phospho-glucomutase activity. Similarly, another transposon-induced mutation eliminates UDP-glucose4 epimerase activity.

LPS is biosynthesized by the initial synthesis of the Lipid A portion followed by the successive addition of the sugar residues of the inner core and then the outer core. It is known that the addition of hexose units, such as glucose and galactose, to the core (e.g., GlcNAc-Hep$_2$(PEA)-KDO$_2$-Lipid A of *Neisseria meningitidis*) is catalyzed by a series of enzymes involved in the biosynthesis. For example, glucose is converted to glucose-6-phosphate by glucokinase. An enzyme, phospho-glucomutase, converts glucose-6-phosphate to glucose-1-phosphate, which is then converted to UDP-glucose by UTP-glucose-1-phosphate-uridyl-tranferase. UDP-glucose is also converted to UDP-galactose by UDP-glucose-4-epimerase. Hexose units from these UDP intermediates are then transferred to the core of the LPS catalyzed by the transferases. The loss of these transfer activities or the enzymes responsible for the generation of UDP-glucose and UDP-galactose result in the preparation of LPS structures containing only the inner core. The pathway necessary for making the core LPS would not be affected by the loss of phospho-glucomutase, UTP-glucose-1-phosphate-uridyl transferase, UDP-glucose-4 epimerase, or the UDP-glucose or UDP-galactose transferases. Therefore, any defect in these enzymes will result in the chain termination of LPS.

Although the LPS of a given gram negative bacteria in any form may be utilized to prepare the present conjugates, it is preferred that the conserved LPS portions of the present invention be de-O-acylated prior to conjugation. The LPS structure can advantageously be de-O-acylated by the mild alkaline hydrolysis thereof with sodium hydroxide as described in, e.g., *J. Biol. Chem.*, 250:1926–1932 (1975) and *J. Biol. Chem.*, 256:7305–7310 (1981) or by mild hydrazine treatment as described in, e.g., *Eur. J. Biochem.*, 177:483–492 (1988). It has been found that de-O-acylating the LPS improves its immunogenicity and reduces its toxicity. Alternatively, the non-toxic LPS portion can be isolated from non-toxic mutants of pathogenic gram negative bacteria, e.g., in the manner described in WO/97/19688.

In producing the antigenic conjugates of the present invention, the conserved LPS portion is linked to a carrier protein via an appropriate linker compound. The use of such linker compounds is known in the art and discussed, e.g., in *Conjugate Vaccines*, Cruise et al., 48–114, Karger Publishing (1989).

For example, reactive groups on the lipid A or inner core portions of the conserved LPS structure can be bound to known heterobifunctional and homobifunctional linking agents. The heterobifunctional linking agents contain heterologous reactive ends and produce intermediates with the conserved LPS. The intermediates are linked at one end to the LPS while the opposing end contains a reactive group. Homobifunctional linking agents also contain two reactive groups, however they are identical. In general, the linking agents connect the conserved LPS portion to the carrier protein via amino, hydroxyl, or carboxyl groups. The amino and hydroxyl group linkages are formed with the saccharides of the lipid A or inner core of the conserved LPS. The carboxyl group linkages are formed with the KDO of the inner core. The opposing end of the linking agent preferably contains a sulfhydryl group for further reaction with the carrier protein.

Suitable linking agents for use in the present invention include, e.g., Sulfosuccinimidyl-6-(3-[2-pyridyldithio]propionamido)-hexanoate (Sulfo-LC-SPDP); succinimidyl-6-(3-[2-pyridyldithio]propionamido)-hexanoate (LC-SPDP); Traut's reagent (2-iminothiolane); N-succinimyl-S-acetyl thioacetate (SATA); N-Succinimidyl-3-(2-pyridyl dithio)propionate (SPDP), succinimidyl acetyl thiopropionate (SATP), succinimidyl-4-(N-maleimido methyl) cyclohexane-1-carboxylate (SMCC), maleimido benzoyl-N-hydroxy succinimide ester (MBS), N-succinimidyl (4-iodoacetyl)aminobenzoate (SIAB), succinimidyl 4-(p-maleimidophenyl)butyrate (SMPB), bromoacetic acid-N-hydroxy succinimide (BANS) ester, 1-ethyl-3-(3-dimethylamino propyl) carbodiimide (EDAC), adipic acid dihydrazide (ADH), cystamine and dithiobis(succinimidyl propionate) (DTSSP).

The conserved portion of the LPS is allowed to react with the linking agent in a non-amino containing buffer solution (such as phosphate buffered saline or sodium biocarbonate) at a neutral to slightly alkaline pH for a suitable period of time (e.g., approximately one hour at room temperature). The intermediate is then removed from unreacted reagent by any suitable means (e.g., gel filtration). The carrier protein is then activated by reaction with a suitable linking agent selected from the group set forth above. The conserved LPS intermediate is then reacted with the activated carrier protein, under suitable conditions, to produce the present conjugates.

In the case of linkage via sulfhydryl groups, the LPS-linking agent intermediate is reacted with a suitable reducing agent or hydroxylamine to reduce the disulfide bond on the linking agent to expose free sulfhydryl groups. Suitable reducing agents include dithiothreitol (DTT) and mercaptoethanol. The sulfhydryl-exposed intermediate is then reacted with an activated carrier protein to provide a thioether-linked covalently bound conjugate.

The formation of an antigenic conjugate via the sulfhydryl groups is illustrated in the schematic set forth below:

(A)

LPS—NH$_2$ + NHS—CO—(CH$_2$)$_5$—NH—CO—CH$_2$—CH$_2$—S—S—Pyridyl $\longrightarrow$ (LC—SPDP)

LPS—NH—CO—(CH$_2$)$_5$—NH—CO—CH$_2$—CH$_2$—S—S—Pyridyl $\xrightarrow{\text{Red. Agent}}$

LPS—NH—CO—(CH$_2$)$_5$—NH—CO—CH$_2$—CH$_2$—SH (B)

Protein-NH$_2$ + NHS—CO—CH$_2$—Br $\longrightarrow$ (Bromoacetic acid N-hydroxy Succinimide) ester Protein-NH—CO—CH$_2$Br (C)

(A) + (B) $\longrightarrow$ LPS—NH—CO—(CH$_2$)$_5$—NH—CO—CH$_2$—CH$_2$—S—CH$_2$—CO—NH-Protein (Protein/LPS Conjugate)

Alternatively, aldehydes may be exposed on the LPS structure by the periodate oxidation of vicinyl hydroxyl groups on the saccharide structures as disclosed in, e.g., Morrison, R. T. and Boyd, R. N., *Organic Chemistry*, Allyn and Bacon, Inc., 875–905 (1966), or by the treatment of LPS containing a non-reducing terminal galactose or N-acetyl galactosamine residue with galactose oxidase to transform the C-6 hydroxyl group to an aldehyde group as disclosed, e.g., in Avigael et al., *J. Biol. Chem.*, 237:2736, (1962). The aldehyde-containing LPS can then be attached to a suitable carrier protein, e.g., by reductive amination.

In another alternative method, the present conjugates may be formed by the linkage of the conserved portion of the LPS and the carrier protein via carboxyl groups on the LPS with the use of a carbodiimide reagent such as 1-ethyl-3-(dimethylaminopropyl)carbodiimide hydrochloride (EDAC). In this method, it is preferred that the conjugates are prepared by linking the carboxyl groups of the LPS saccharide to the carboxyl groups of the carrier protein. In this case, the conserved LPS is first reacted with a suitable linker compound, such as adipic acid dihydrazide (ADH) in the presence of EDAC. The carrier protein may then be reacted with the ADH-LPS intermediate in the presence of an appropriate linker compound, such as EDAC. A carboxyl-linked conjugate is obtained.

The formation of an antigenic conjugate via linkage of the carboxyl groups is illustrated in the schematic set forth below.

(A)

LPS—COOH +

NH$_2$NH—CO—(CH$_2$)$_4$—CO—NH—NH$_2$ $\xrightarrow{\text{EDAC/NHS}}$ (ADH)

LPS—CO—NH—NH—CO—(CH$_2$)$_4$—CO—NH—NH$_2$ (B)

(A) + Protein-COOH $\xrightarrow{\text{EDAC/NHS}}$

LPS—CO—NH—NH—CO—(CH$_2$)$_4$—CO—NH—NH—CO-Protein (Carboxyl-linked-ADH conjugate)

NHS = N-hydroxy succinimide

In another alternative embodiment, the present conjugates may be formed by linking the carboxyl groups of the LPS saccharide to the amino groups of a carrier protein. In this case, the conserved LPS is first reacted with cystamine in the presence of EDAC. The sulfhydryl group from the cystamine-LPS intermediate is exposed by a reducing agent, such as dithiothritol and finally reacted with a bromoacetylated carrier protein.

Carrier proteins useful in the preparation of the present antigenic conjugates include bacterial toxins and toxoids (e.g., tetanus toxin or toxoid, diptheria toxin or toxoid, non-toxic mutants of diptheria toxin CRM-$_{197}$ (as described, e.g., in *Immunochem.*, 9:891–906 (1972)), pseudomonas exotoxin A, cholera toxin or toxoid, Group A streptococcal toxins, pneumolysin of *Streptococcus pneumoniae*, etc.); filamentous haemagglutinin (FHA) or FHA fragment(s) of *Bordetella pertussis*; pili or pilins of *Neisseria gonorrhoeae*; pili or pilins of *Neisseria meningitidis*; bacterial outer membrane proteins (e.g., outer membrane protein complexes of *Neisseria meningitidis* (e.g., such as class 1 outer membrane protein and class 3 outer membrane protein of *Neisseria meningitidis*)); outer membrane proteins of *Neisseria gonorrhoeae*; C5A peptidase of Streptococcus; and ubiquitous surface protein of *Moraxella catarrhalis*. The preferred carrier protein is CRM-$_{197}$.

Vaccines containing the antigenic conjugates of the present invention may advantageously contain various adjuvants which are known to augment the immune response to the vaccine antigen. It is believed that such adjuvants increase the antibody response by the non-specific stimulation of the patient's immune system. The use of adjuvants is well known in the art and is described, e.g., in "Vaccine Design: The Subunit and Adjuvant Approach", Powell et al., Plenum Press (1995). Examples of adjuvants suitable for use in vaccines containing the present conjugates include: aluminum phosphate, aluminum hydroxide, monophosphoryl lipid A, 3-deacylated monophosphoryl lipid A, QS-21(as disclosed in *J. Immunol.*, 146:431–437 (1991)), as well as various detergents (e.g., Triton™ X 100, zwittergents and deoxycholate) in combination with the aluminum compounds. In general, the antibody response to the present conjugates is substantially increased by the inclusion of one or more adjuvants in the vaccine.

Many methods are known to be suitable for the administration of a vaccine formulation to individuals in need thereof. Suitable methods of administration include, intradermal, intramuscular, intraperitoneal, intravenous, intraarterial, vaginal, subcutaneous, ocular, intranasal, and oral administration.

The vaccine formulations containing the present antigenic conjugates may comprise the conjugate in a physiologically acceptable carrier, such as isotonic solution, saline, phosphate buffered saline, etc. The vaccine formulation is administered to an individual in a prophylactically effective amount.

Due to their cross reactivity to a number of different or heterologous bacterial species, the antigenic conjugates of the present invention are effective as components of vaccines to produce an immunologic reaction in humans to disease caused by LPS-producing bacterial organisms. Vaccines containing the present conjugates may be prepared by methods and with materials which are known to those skilled in the art.

Antibodies generated by the present conjugates may be used to examine whether an infection has been caused by an LPS-producing bacterial organism by testing the blood samples, body fluids or biopsy samples of the infected individual. Therapeutic and prophylactic applications include the use of present vaccines as well as the antibodies obtained therewith. Active immunization with the antigenic conjugates of the present invention may be useful for the prevention of bacterial infection or diseases.

The vaccines of the present invention are also useful for the prophylaxis of septic shock caused by various gram negative bacteria, e.g., Salmonella, *Escherichia coli*, Neisseria, Haemophilus, Shigella, Klebsiella and Pseudomonas. It has been discovered that, in certain cases, a significant amount of LPS is released from the dead cells of the bacteria following therapy with conventional antibiotics *J. Infect. Dis.*, 157:567–568 (1988). This can lead to endotoxin-induced complications in these patients.

One approach of preventing septic shock and its related complications is the administration to the patient of monoclonal or polyclonal antibodies to the common core region of the LPS of the potentially involved bacteria. Such antiserum may prevent the toxic effects of excessively produced LPS by the bacterial organism. The potential of LPS antibody therapy in animal models using LPS produced by mutants of *Escherichia coli* or *Salmonella minnesota* immunogens have been reviewed by Applemelk and Cohen in, "Bacterial Endotoxic Lypopolysaccharides—Vol. II", *Immunopharmacology and Pathology*, CRC Press, (1992).

The present invention will now be illustrated by the following specific, non-limiting examples.

EXAMPLES

Selection of Bacteria and Growth Conditions

A Tn916 induced LPS mutant of *Neisseria meningitidis* strain NMB-R6 was constructed according to the procedure set forth in Zhou et al., *J. Biol. Chem.* 269:11162–11169 (1994). This strain is a phenotypically stable mutant which expresses LPS with a molecular mass of approximately 3.1–3.2 KDa. It has been shown that the inability of this mutant strain to convert glucose-6-phosphate to glucose-1-phosphate results in a truncated LPS portion containing only the conserved core LPS structure of *Neisseria meningitidis*. The structure of the LPS produced by this mutant strain has been identified as GlcNAc-Hep$_2$phosphoethanolamine-KDO$_2$-LipidA.

This mutant strain was grown on GC agar plate media for 6 hrs at 35° C. in 5% CO$_2$. Cells from the solid agar culture were then grown for 18 hours in a supplemented liquid media which contained 0.2% yeast extract dialysate. The culture was then transferred to Fembach flasks and grown for an additional 18–24 hours. The cells were then heat killed and harvested by centrifugation for the purification of the LPS structure.

LPS Purification

LPS was extracted from the NMB-R6 cells by the hot phenol-water extraction method described in Wu et al., *Anal. Chem.*, 160:298–289 (1987) and purified via ultracentrifugation. More specifically, cell pellets were suspended in 3 volumes (3 ml buffer/gm wet weight) of phosphate buffer (pH 7.1) containing 5 mM EDTA and 0.02% sodium azide. Lysozyme (available from Sigma Chemical Co.), at a concentration of 2 mg/ml, was then added to the suspension. This mixture was then digested overnight at 4° C. The suspension was brought to 37 C. and further digested with RNAse and DNAse at a concentration of 100 μg/ml for 3 hours. The digest was then brought to 70° C. and an equal volume of phenol at 70° C. was added thereto. This mixture was extracted for a period of 15 minutes, and the suspension was then cooled to 4° C. and centrifuged at 10,000 g for 30 minutes. The aqueous phase was recovered and the phenol phase was reextracted with an equal volume of water at 70° C. for 15 minutes. This phase was then centrifuged at 10,000g for 30 minutes and the aqueous phase was then separated. Sodium acetate was added to the combined aqueous supernatants at a concentration of 5 mg/ml. Two volumes of ice cold acetone were then added to this mixture and the LPS was allowed to precipitate overnight at 4° C. The precipitated LPS was separated by centrifugation at 10,000 g for 30 minutes. The recovered LPS was suspended in sterile water and subjected to three rounds of ultracentrifugation at 105,000 g for three hours. The final pellet was suspended in a small volume of sterile water for the subsequent experiments. Typically, 3mg of LPS was purified from 1 gm wet weight of the NMB-R6 cells.

Conjugation to Carrier Protein, $CRM_{197}$

The LPS purified in the manner described above, was then de-O-acylated by the reaction thereof with 45 mM of NaOH at 80° C. for 20 minutes. The de-O-acylated material was then neutralized with HCl and purified by gel filtration on a BiogeL P6 column using 0.1 M $NaHCO_3$ as an eluant. The de-O-acylated LPS (referred to hereinafter as "DeA-LPS") was then conjugated to the carrier protein $CRM_{197}$ by linking the amino groups of the saccharides on the conserved LPS structure to the amino groups of the carrier protein utilizing the procedure described below. $CRM_{197}$ is a non toxic mutant protein of diphtheria toxin and has been used as a carrier protein for the commercial production of glycoconjugate vaccines for human use.

Long chain sulfo-N-succinimidyl-3-(2-pyridyldithio)-propionate (sulfo LC-SPDP available from the Pierce Chemical Company) was used to thiolate the primary amino group(s) of the DeA-LPS. The sulfo LC-SPDP was added to 15 mg of the LPS in 0.1 M $NaHCO_3$ (pH 7.9) at a ratio of 1:1 (w/w). This mixture was then incubated for an hour at room temperature. At the end of the reaction, the mixture was purified on a BiogeL P6 column equilibrated in 0.1 M $NaHCO_3$. The recovered fractions were assayed for KDO according to the procedure set forth in Keleti and Lederer, *Biochem. Biophys.*, 74:443–450 (1974) and the fractions containing the KDO were pooled. The N-pyridyl disulfides present in the SPDP derivatives of the LPS were reduced with 50–100 mM dithiothreitol (DTT) and gel filtered on a BiogeL P6 column as described above. The thiolated material containing the KDO positive fractions were again pooled. Thiolation of the oligosaccharides of the DeA-LPS was monitored in accordance with the reaction described in Ellman, G. L., *Arch. Biochem. Biophys.*, 74:443–450 (1958). 0.1 ml of the material was mixed with 0.1 ml of Ellman reagent (i.e., 40 mg of 5,5'-dithiobis(2 nitrobenzoic) acid in 10 ml of pH 8.0 phosphate buffer). After 15 minutes of incubation, the absorbance was 412 nm. Cysteine was used as the standard sulfhydryl reagent.

The $CRM_{197}$ carrier protein was bromoacetylated according to the procedure described in Bernatowitz and Matsueda, *Anal. Biochem.*, 155:95–102 (1986). Bromoacetic acid-N-hydroxy succinimide ester (available from Sigma Chemical Co.) in 100 mg/ml of dimethyl formamide was added dropwise to 3 ml of the protein (in 0.1M $NaHCO_3$) at a ratio of 1:1 (w/w) at 4° C. The solution was mixed and incubated for 1 hour at room temperature. The reaction mixture was then gel filtered on a BiogeL P6 column as described above and the void fractions containing the bromoacetylated protein were pooled. Derivatization of amino groups on the carrier protein to the bromoacetyl groups was monitored by a decrease in the amount of free amino groups.

The bromoacetylated $CRM_{197}$ in 0.1 M $NaHCO_3$ was then added to the thiolated DeA-LPS at a 1:1.5 ratio of protein to LPS (w/w) in 0.1 M $NaHCO_3$. The reaction mixture was incubated overnight at 4° C. The final conjugate (hereinafter referred to as "DeA-LPS-SPDP-CRM") was purified by gel filtration on a BiogeL-P30 (Bio-Rad) column equilibrated in 0.1 M $NaHCO_3$/1 mM EDTA, pH7–9.

Immunogenicity Determination

The immunogenicity of the DeA-LPS-SPDP-CRM conjugate prepared above was determined in Swiss Webster mice according to the following procedure. Groups of 6–8 week old female mice, 10 per group, were immunized subcutaneously with 10 pg LPS, 10 µg DeA-LPS, 10 µg DeA-LPS-SPDP (i.e., the unconjugated intermediate) and 10 µg of the DeA-LPS-SPDP-CRM conjugate. 10 µg $CRM_{197}$ was also administered to the mice to serve as a control. Each of these immunogens further contained 20 µg of QS-21 (available from Aquila) as an adjuvant in a final volume of 0.1 ml containing phosphate buffered saline (PBS), per dose. An additional group was immunized with 10 µg of LPS without the QS21 adjuvant. The animals were immunized at weeks 0, 3, and 6 and blood samples were taken prior to each immunization for antibody determination. Blood samples were further taken at week 8 for antibody determination.

LPS antibody levels were determined by the Enzyme Linked Immunosorbent Assay (ELISA) procedure against purified LPS from R6 and the other wild type and immunotype specific *Neisseria meningitidis* strains identified below. The immunotype specific strains were obtained from Walter Reed Army Medical Center, Washington. LPS was purified from these strains by the hot phenol-water extraction method described above.

The purified LPS was diluted in endotoxin-free PBS to the following concentrations: 10 µg/mL for *Neisseria meningitidis* strains A1, H44/76, 2996 and Immunotypes L1, L2, L3, L4, L5, L6, L7, L8, L10, L11 and L12; and 2.5 µg/mL for the R6 strain. Polystyrene microtiter plates were coated with 100 µL per well of the diluted LPS-containing mixtures and incubated for 3 hours at 37° C. followed by overnight storage at 4° C. The unbound LPS was then removed from the plates by suction utilizing an automatic plate washer. 150 µL per well of PBS/0.1% gelatin was then added to the plates and the plates were then incubated for 60 minutes at 37° C. Following this incubation, and between all subsequent steps, the plates were washed with a mixture of PBS and 0.1% TWEEN-20 using an automatic plate washer.

Test mouse sera was serially diluted in a mixture of PBS, 0.05%, TWEEN-20 and 0.1% gelatin. 100 µL per well of the dilution was added to the plates. The plates were incubated for 60 minutes at 37° C. Goat anti-mouse IgG alkaline phosphatase (from Southern Biotechnology), diluted in a mixture of PBS and 0.5%, TWEEN-20, was then added in an amount of 100 µL per well and incubated for 60 minutes at 37° C. The color was developed using 100 µl of a 1 mg/ml solution of p-nitrophenol phosphate in a diethanolamine buffer. These materials were allowed to react for 60 minutes at room temperature, after which the reaction was stopped by the addition of 50 µL per well of 3N NaOH. Absorbance values were determined using an automated ELISA reader with a 405 nm test and 690 nm reference filter.

The data demonstrating the immunogenicity of the DeA-LPS-SPDP-CRM conjugate against homologous LPS from the R6 strain at weeks 0, 3, 6, and 8 is shown in Table 1. As can be seen from this data, the conjugate produced a significant boostable IgG antibody response.

TABLE 1

| | IgG antibody response to R6 LPS at week* | | | |
|---|---|---|---|---|
| Immunogen | 0 | 3 | 6 | 8 |
| LPS | <50 | 365 | 769 | 17,633 |
| LPS + QS-21 | <50 | 1,079 | 24,225 | 84,491 |
| DeA-LPS + QS-21 | ND | ND | ND | 221 |
| DeA-LPS-SPDP-CRM$_{197}$ + QS-21 | <50 | 203 | 6,647 | 56,062 |
| CRM$_{197}$ + QS-21 | <50 | <50 | <50 | <50 |

DeA-LPS: DeO-acylated LPS, unconjugated
DeA-LPS-SPDP: Activated deO-acylated LPS, unconjugated
DeA-LPS-SPDP-CRM: DeO-acylated LPS conjugated to CRM$_{197}$ by SPDP
ND = Not Done
*The value represents end point dilutions at which the diluted serum gives a value of an O.D. of 0.1.

The cross reactive immunogenicity of the conjugate produced in the present examples to heterologous LPS of various strains of Neisseria meningitidis was also examined according to the procedure described above and the data obtained is set forth in Table 2. The strains examined were: A1, R6, H44/76, 2996, Immunotypes L1, L2, L3, L4, L5, L6, L7, L8, L10, L11, and L12. As can be seen in Table 2, the LPS-protein conjugate produced a significant antibody response, particularly in comparison to the unconjugated LPS.

TABLE 2

| Strains | DeA-LPS-SPDP | DeA-LPS-SPDP-CRM$_{197}$ |
|---|---|---|
| R6 | 443 | 33,067 |
| A1 | <100 | 36,923 |
| H44/76 | 147 | 24,811 |
| 2996 | <100 | 11,467 |
| L1 | <100 | 11,963 |
| L2 | 350 | 4500 |
| L3 | 304 | 7,936 |
| L4 | 412 | 12,820 |
| L5 | 259 | 16,251 |
| L6 | 129 | 11,600 |
| L7 | <100 | 16,533 |
| L8 | 232 | 16,278 |
| L10 | 141 | 11,982 |
| L11 | <100 | 3200 |
| L12 | 142 | 4,870 |

DeA-LPS-SPDP: Activated deO-acylated LPS, unconjugated
DeA-LPS-SPDP-CRM: DeO-acylated LPS conjugated to CRM$_{197}$ by SPDP The cross reactivity of anti-LPS conjugate antisera (the antisera against DeA-LPS-SPDP-CRM) was further examined by western blot analysis against purified LPS from various strains of several gram negative bacteria. Purified LPS samples of Neisseria meningitidis, Haemophilus influenzae, Neisseria gonorrhoeae, Moraxella catarrhalis, and Helicobacter pylori were first digested with protease and subjected to a standard SDS-PAGE (18%) separation procedure. The samples were then transferred to nitrocellulose membrane by standard western blot procedure. The membrane was blocked with 3% Bovine Serum Albumin (BSA) in a mixture of PBS/0.05% TWEEN-20 for 30 min. and reacted with 1:100 dilution of test mouse sera. The blots were then washed with a mixture of PBS/0.05% TWEEN 20 and incubated with goat anti-mouse Ig alkaline phosphatase diluted in a mixture of PBS/0.05% TWEEN 20. Following the washing procedure, the blots were developed using 5-bromo-4-chloro-3-indolylphosphate (BCIP)/nitroblue tetrazolium concentrate (NBT) phosphatase substrate system as described by the manufacturer (Kirkegaard and Perry Laboratories, Inc., MD). The development procedure comprised mixing one part each of the BCIP and NBT concentrates with ten parts of Tris buffer solution in a glass container and adding these mixtures to the blots. After color development, the reaction was stopped by rinsing the blots with reagent quality water.

Figure 4:
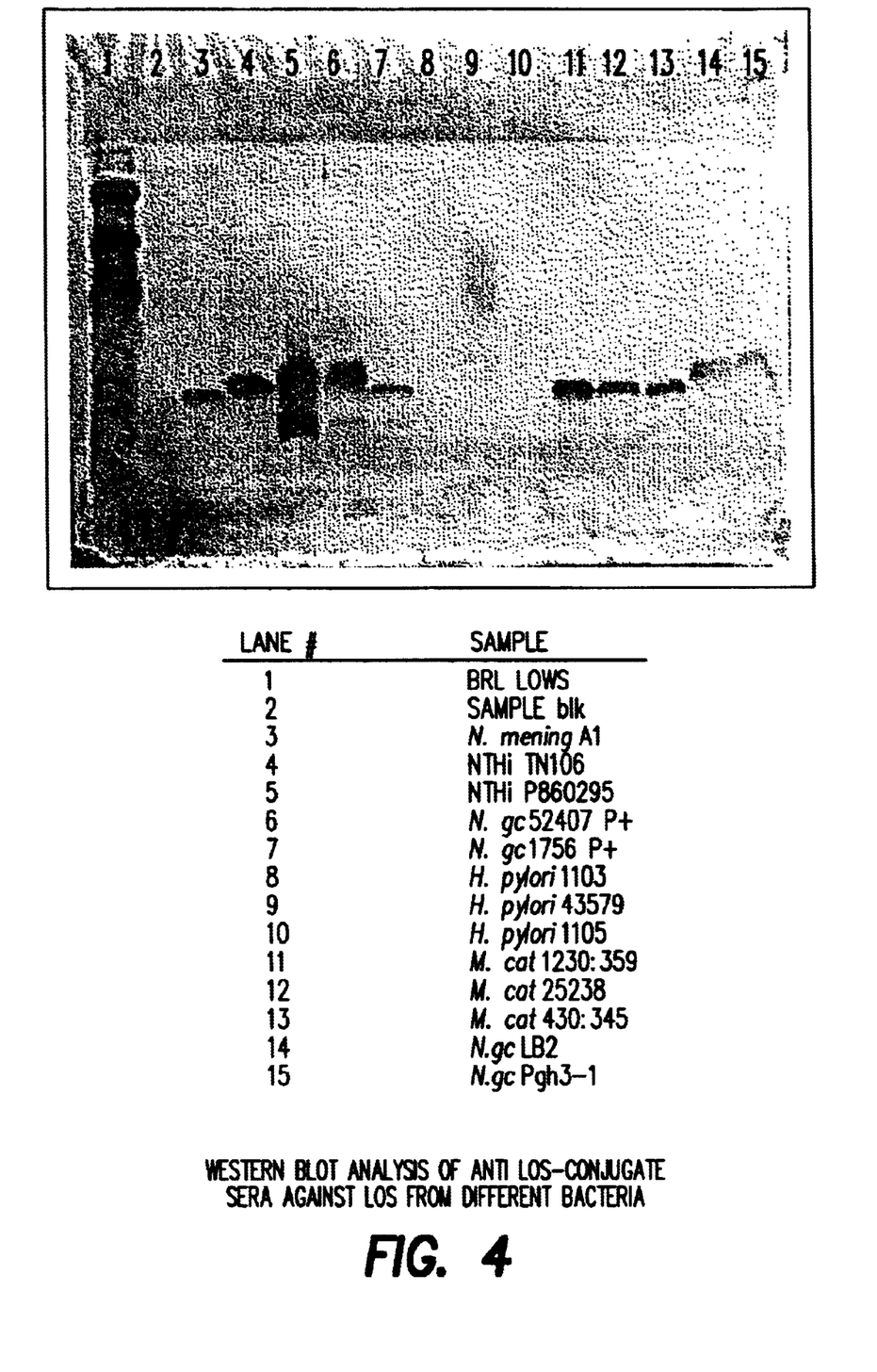
FIG. 4 shows the Western Blot analysis of the activity of various conjugates against the anti-sera of various bacteria.

As can be seen in FIG. 4, with the exception of Helicobacter pylori, the LPS of each of the organisms reacted strongly with the antisera. Although less intense, it appears that there was also a slight cross reactivity to the LPS from Helicobacter pylori. These results clearly indicate that the antibodies generated from the LPS conjugate of Neisseria meningitidis cross reacted with a number of other gram negative organisms.

The bactericidal activities of the antisera were further examined using the R6 strain, the group A strain (A1) and two group B strains: H44/76 and 2996. Serum samples were diluted in 5 $\mu$l of PCM (PBS containing Ca and Mg) and this dilution was added to reaction mixtures containing 2–5×10$^3$ Neisseria meningitidis (10 $\mu$l), human serum complement (10 $\mu$l) and PCM (25 $\mu$l). This mixture was then incubated for 45 min. at 36° C. in 5% CO$_2$. The reaction was then terminated by dilution with 200 $\mu$l of PBS. Two aliquots (50 $\mu$l) of the mixture were then plated onto GC agar plates and further incubated in 5% CO$_2$ at 36° C. The bactericidal titers (BC50) were then determined. Bactericidal titers represent the reciprocal of the dilution of antiserum that kills 50% of the colony forming Neisseria meningitidis in the assay. The data is set forth below in Table 3.

As can be seen in Table 3, the conjugate antisera was able to kill bacteria expressing different LPS immunotypes. Such conjugates induced boostable T cell dependent IgG response.

TABLE 3

| | BC$_{50}$ titers | | | |
|---|---|---|---|---|
| Immunogen | Strain H44/76 | Strain 2996 | Strain A1 | *Strain R6 |
| LPS | <50 | <50 | <50 | <50 |
| DeA-LPS-SPDP | <50 | <50 | <50 | ND |
| DeA-LPS-SPDP-CRM$_{197}$ | 50 | 70 | 350 | <50 |
| Normal mouse serum | <50 | <50 | <50 | <50 |

*Positive control antisera (mouse anti-A1 LPS) was used in assay and gave a titer of 100.
ND = Not Done
DeA-LPS-SPDP: Activated deO-acylated LPS, unconjugated
DeA-LPS-SPDP-CRM: DeO-acylated LPS conjugated to CRM$_{197}$ by SPDP Accordingly, it can readily be seen from the data set forth above that the antigenic conjugates of the present invention produce a significant immune response to the LPS of a given bacterial organism. Moreover, this data demonstrates that the present conjugates induce a cross reactive response to different strains of the bacterial organism as well as to different species of bacterial organisms.

The present invention may be embodied in other specific forms without departing from the spirit and essential attributes thereof and accordingly, reference should be made to the appended claims, rather than to the foregoing specification, as indicating the scope of the invention.

What is claimed is:

1. An antigenic conjugate comprising a carrier protein covalently bonded to the conserved portion of an isolated lipopolysaccharide of *Neisseria meningitidis*, wherein said conserved portion of the lipopolysaccharide comprises GlcNAc-Hep$_2$phosphoethanolamine-KDO$_2$-Lipid A, said conjugate eliciting a cross reactive immune response against heterologous strains of *Neisseria meningitidis*.

2. The antigenic conjugate as in claim 1, wherein said lipopolysaccharide is de-O-acylated.

3. The antigenic conjugate as in claim 1, wherein said carrier protein is selected from the group consisting of tetanus toxin or toxoid, diptheria toxin or toxoid, mutant of diptheria toxin CRM$_{197}$, pseudomonas exotoxin A, cholera toxin or toxoid, Group A streptococcal toxins, pneumolysin of *Streptococcus pneumoniae*, filamentous haemagglutinin (FHA), FHA fragments of *Bordetella pertussis*; pili or pilins of *Neisseria gonorrhoeae*, pili or pilins of *Neisseria meningitidis*; outer membrane proteins of *Neisseria meningitidis*, outer membrane proteins of *Neisseria gonorrhoeae*; C5A peptidase of Streptococcus and surface protein of *Moraxella catarrhalis*.

4. The antigenic conjugate as in claim 1, wherein said carrier protein is linked to said conserved portion of the lipopolysaccharide with a compound selected from the group consisting of Sulfosuccinimidyl-6-(3-[2-pyridyldithio]propionamido)-hexanoate (Sulfo-LC-SPDP); succinimidyl-6-(3-[2-pyridyldithio]propionamido)-hexamnoate (LC-SPDP); Traut's reagent (2-iminothiolane); N-succinimyl-S-acetyl thioacetate (SATA); N-Succinimidyl-3-(2-pyridyl dithio) propionate (SPDP), succinimidyl acetyl thiopiopinate (SATP), succinimidyl-4-(N-maleimido methyl) cyclohexane-1-carboxylate (SMCC), maleimido benzoyl-N-hydroxy succinimide ester (MBS), N-succinimidyl (4-iodoacetyl)aminobenzoate (SIAB), succinimidyl 4-(p-maleimidophenyl)butyrate (SMPB), bromacetic acid-N-hydroxy succinimide (BANS) ester, 1-ethyl-3-(3-dimethylamino propyl) carbodiimide (EDAC), adipic acid dihydrazide (ADH), and cystamine and dithiobis (succinimidyl propionate) (DTSSP).

5. An antigenic conjugate comprising the carrier protein diptheria toxin CRM$_{197}$ covalently bonded to the conserved portion of an isolated lipopolysaccharide of *Neisseria meningitidis* with long chain N-succinimidyl-3-(2-pyridyldithio)-propionate, and bromacetic acid-N-hydroxysuccinimide ester, wherein said conserved portion of the lipopolysaccharide comprises GlcNAc-Hep$_2$phosphoethanolamine-KDO$_2$-Lipid A, said conjugate eliciting a cross reactive immune response against heterologous strains of *Neisseria meningitidis*.

6. A vaccine formulation comprising a prophylactically effective amount of the antigenic conjugate of claim 1.

7. A vaccine formulation comprising an a prophylactically effective amount of the antigenic conjugate of claim 5.

8. The antigenic conjugate as in claim 5, wherein said conserved portion is capable of substitution by phosphoethanolamine.

* * * * *